United States Patent [19]

Eicher et al.

[11] Patent Number: 5,300,709
[45] Date of Patent: Apr. 5, 1994

[54] PROCESS FOR WORKING UP A HYDROGEN FLUORIDE PHASE FROM A FLUORINATION REACTION MIXTURE

[75] Inventors: Johannes Eicher, Garbsen; Werner Rudolph, Hanover; Bernhard Schulte, Bad Rappenau, all of Fed. Rep. of Germany

[73] Assignee: Solvay Fluor and Derivate GmbH, Hanover, Fed. Rep. of Germany

[21] Appl. No.: 3,001

[22] Filed: Jan. 11, 1993

[30] Foreign Application Priority Data

Jan. 15, 1992 [DE] Fed. Rep. of Germany ....... 4200792

[51] Int. Cl.⁵ ............................................. C07C 17/08
[52] U.S. Cl. .................................................. 570/164
[58] Field of Search ............... 570/164, 177, 178, 165, 570/166, 167

[56] References Cited

U.S. PATENT DOCUMENTS

| | | | |
|---|---|---|---|
| 2,640,086 | 5/1953 | Baldwin | 570/165 |
| 3,047,641 | 7/1962 | Neill et al. | 570/165 |
| 3,919,399 | 11/1975 | Schabacher et al. | 423/488 |
| 4,460,551 | 7/1984 | Bose et al. | 423/166 |

FOREIGN PATENT DOCUMENTS

| | | |
|---|---|---|
| 1264428 | 3/1968 | Fed. Rep. of Germany ...... 570/165 |
| 2209960 | 9/1973 | Fed. Rep. of Germany . |
| 4005945 | 8/1991 | Fed. Rep. of Germany . |
| WO 82/03848 | 11/1982 | World Int. Prop. O. . |

OTHER PUBLICATIONS

Weissberger Separation and Purification vol. III Part 1 2nd ed pp. 809-811.

*Primary Examiner*—Alan Siegel
*Attorney, Agent, or Firm*—Evenson, McKeown, Edwards & Lenahan

[57] ABSTRACT

A process for working up the hydrogen fluoride phase of reaction mixtures from fluorination reactions comprising contacting the hydrogen fluoride phase with oleum in order to obtain dried hydrogen fluoride, which can be recycled to the fluorination reaction.

8 Claims, 1 Drawing Sheet

PROCESS FOR WORKING UP A HYDROGEN FLUORIDE PHASE FROM A FLUORINATION REACTION MIXTURE

BACKGROUND OF THE INVENTION

The present invention relates to a process for working up the hydrogen fluoride phase of reaction mixtures from fluorination reactions.

Fluorine-containing hydrocarbons are produced on a large scale by reacting halogenated hydrocarbons with hydrogen fluoride. Usually one starts with chlorine-containing hydrocarbons. In addition to fully halogenated carbon compounds, compounds which also contain hydrogen in addition to fluorine (and optionally chlorine) may of course also be used or produced. Alkenes may for instance also be used as starting materials for the preparation of fluorine-containing hydrocarbons, so that hydrogen fluoride addition also takes place. Compounds of this type have become important as replacements for fully halogenated carbon compounds.

A process of this type is described in published German Patent Application No. DE 4,005,945. Ethane derivatives containing trifluoromethyl groups, such as $CF_3CHCl_2$, are prepared from halogen-containing alkenes or alkanes, with a halogen-fluorine exchange and optionally addition of hydrogen fluoride. In the course of working-up the reaction mixture, volatile reaction products are first collected in a phase separator. In so doing, two separate phases are obtained. The heavy phase contains predominantly organic compounds, in particular the desired reaction product. The lighter phase contains predominantly hydrogen fluoride and water. The hydrogen fluoride phase is recycled to the fluorination reaction. Any readily volatile constituents released in the phase separator are passed through a gas scrubber. The disadvantage of this process is that the water contained in the hydrogen fluoride phase is recycled.

SUMMARY OF THE INVENTION

It is the object of the present invention to provide a process for producing fluorine-containing hydrocarbons in which the usability of the hydrogen fluoride phase which has been separated from the organic phase is improved.

This and other objects of the invention are achieved by providing a process for working up a hydrogen fluoride phase recovered from a fluorination reaction mixture, comprising contacting the hydrogen fluoride phase with oleum in order to separate water, and recycling the resulting hydrogen fluoride to the fluorination reaction.

The process according to the invention for working up the hydrogen fluoride phase of reaction mixtures from fluorination reactions provides for the hydrogen fluoride phase to be contacted with oleum (also known as fuming sulfuric acid) in order to remove water, and for the resulting hydrogen fluoride to be recycled into the fluorination reaction.

The contacting step preferably takes place by countercurrent flow through a packed column, but may also take place by shaking the hydrogen fluoride phase with oleum or by passing the hydrogen fluoride phase through oleum.

After contact with the oleum, the hydrogen fluoride may, if desired, be fractionated further in order to separate any sulfuric acid or oleum which has been entrained therein. This may take place in a separate rectifying column. Advantageously, however, a packed column with a rectifying column placed on top is used. The hydrogen fluoride phase is then introduced into the packed column and dried with oleum at elevated temperature, for example at temperatures of 160° C. to 200° C. The hot hydrogen fluoride gases, which may be contaminated with entrained sulfuric acid or oleum, rise into the rectifying column. Sulfuric acid and other high-boiling substances are separated from the hydrogen fluoride in the rectifying column, and pure hydrogen fluoride is withdrawn at the head of the column.

The hydrogen fluoride (HF) fraction drawn off at the top may still contain hydrogen chloride (HCl) and low-boiling organic constituents, and may be recycled directly. The dried hydrogen fluoride fraction which is drawn off contains only very little, if any, water.

The oleum used may contain more or less $SO_3$. Advantageously, oleum is used which has an $SO_3$ content of between 1 and 40% by weight, relative to the $H_2SO_4$ set as 100% by weight.

The spent oleum from the drying step may be regenerated by adding $SO_3$ and/or oleum. However, the spent oleum may also be used in a process for preparing hydrogen fluoride by reacting fluorite ($CaF_2$) with sulfuric acid or oleum. It is known that hydrogen fluoride can be prepared by reacting fluorite with sulfuric acid or oleum, thereby forming calcium sulfate and hydrogen fluoride. This usually takes place at a very elevated temperature (200° C. or more) in a rotary furnace. In accordance with a preferred embodiment of the process of the invention, the water-laden oleum or the resulting sulfuric acid is used to replace part of the sulfuric acid and/or oleum required for reacting fluorite with sulfuric acid.

Of course, part of the spent oleum resulting from the drying of the hydrogen fluoride may also be recycled after replenishment with $SO_3$ and/or oleum, and the other part may be used to prepare hydrogen fluoride from calcium fluoride.

The pressure in the rectifying column is desirably in the range from 1 to 2 bar, preferably in the range from 1.5 to 2 bar.

The temperature of the rectifying column is advantageously controlled such that there is a temperature of 10 to 20° C. in the upper region (column head) and a temperature of 160 to 200° C. in the lower region (column base) of the column.

The working-up process according to the invention is utilized in processes for preparing hydrocarbons containing fluorine and optionally other halogens. Such processes for preparing fluorine-containing hydrocarbons comprise a halogen-fluorine exchange using excess hydrogen fluoride, working up the reaction mixture to form two phases, one phase of which consists essentially of organic compounds and the other phase of which is a hydrogen fluoride phase, separating the hydrogen fluoride phase from the other phase and working up and recycling the hydrogen fluoride phase according to the process of the present invention.

BRIEF DESCRIPTION OF THE DRAWING

The process will be explained in further detail hereinafter with reference to the accompanying Figure which is a schematic representation of an apparatus for carrying out the process of the invention.

DETAILED DESCRIPTION OF PREFERRED EMBODIMENTS

Figure 1:
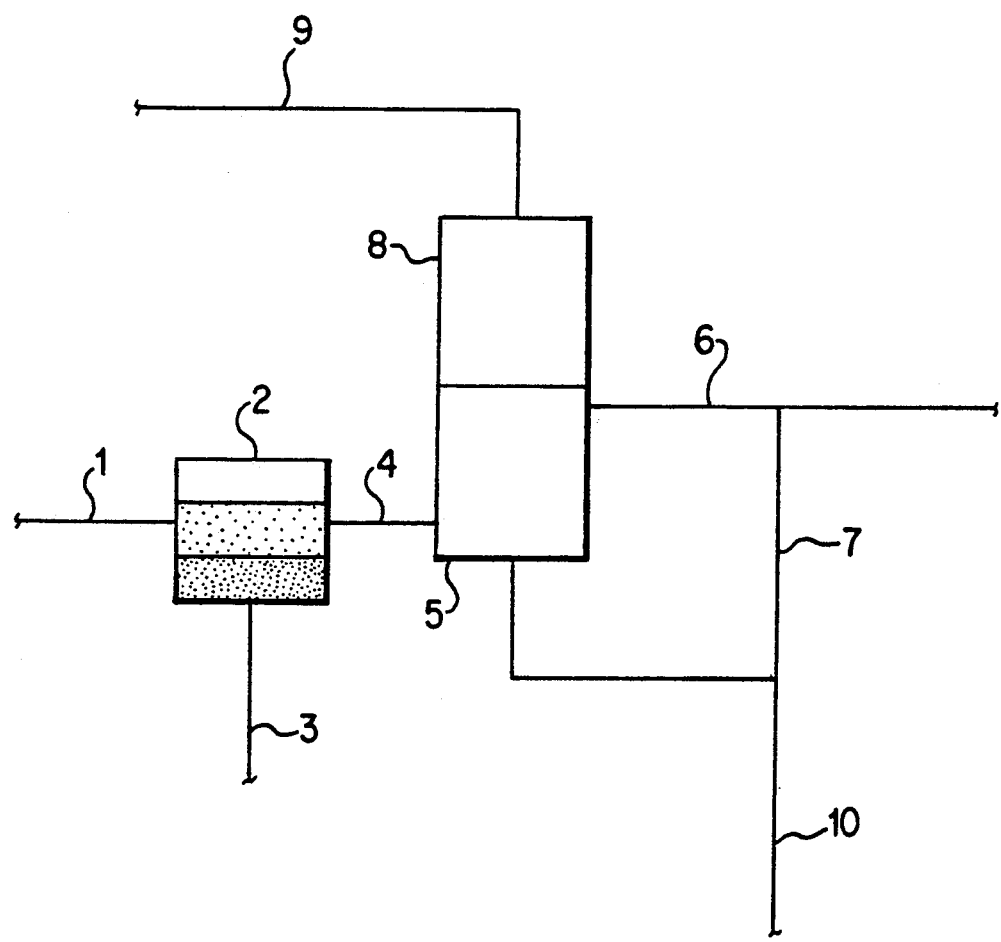

The working-up process according to the invention will now be described with reference to an illustrative preferred embodiment for the preparation of $CF_3CHCl_2$ from tetrachloroethylene and hydrogen fluoride. The volatile constituents obtained by reacting tetrachloroethylene with hydrogen fluoride (essentially HCl, HF, organic compounds and water) were introduced via line 1 into a phase separator 2 and condensed. Two phases were formed. The heavier phase consisted essentially of $CF_3CHCl_2$, partially fluorinated compounds and starting compound. This heavier phase was discharged from the phase separator 2 via line 3 and separated further by distillation.

The lighter phase, referred to hereinafter as the hydrogen fluoride phase, consisted essentially of HF, HCl, water and readily volatile organic compounds. This hydrogen fluoride phase was introduced into a drying column 5 via line 4. Oleum (40% by weight $SO_3$ relative to the $H_2SO_4$ set as 100% by weight) was introduced into the drying column 5 via line 6. The hydrogen fluoride phase and the oleum were passed through the column in countercurrent relation. A packing in the column was used to intensify the contact between the oleum and the hydrogen fluoride phase in the column. A portion of the sulfuric acid used for drying was transferred into the hydrogen fluoride recovery from fluorite stage (line 10). The remainder was introduced via line 7 into line 6, mixed therein with fresh oleum, and then recycled into the drying column 5. The hydrogen fluoride, which was largely freed of water, rose into the rectifying column 8 and was freed therein from entrained sulfuric acid and oleum. The rectified hydrogen fluoride was recycled via line 9 back to the fluorination apparatus.

Although the use of the process of the invention for working up the hydrogen fluoride phase separated from the organic phase obtained in the preparation of $CF_3CHCl_2$ has been described above, it will be apparent to a person skilled in the art that the working-up process of the invention may also be used in other processes for preparing fluorine-containing hydrocarbons in which hydrogen fluoride phases containing low-boiling compounds and water are produced.

The foregoing description and examples have been set forth merely to illustrate the invention and are not intended to be limiting. Since modifications of the described embodiments incorporating the spirit and substance of the invention may occur to persons skilled in the art, the scope of the invention should be construed to include all variations falling within the ambit of the appended claims and equivalents thereof.

What is claimed is:

1. A process for working up a hydrogen fluoride phase recovered from a reaction mixture from a fluorination reaction, said process comprising contacting the hydrogen fluoride phase with oleum at a temperature of from 160° C. to 200° C. in order to separate water, and recycling the resulting hydrogen fluoride to the fluorination reaction.

2. A process according to claim 1, wherein said contacting step is carried out by countercurrent flow in a packed column.

3. A process according to claim 1, further comprising regenerating spent oleum from the contacting step by adding $SO_3$, and recycling regenerated oleum to the drying step.

4. A process according to claim 1, further comprising reacting spent oleum from the contacting step with fluorite to produce hydrogen fluoride.

5. A process according to claim wherein said contacting step is performed with oleum containing from 1 to 40 parts by weight $SO_3$ per 100 parts by weight $H_2SO_4$.

6. A process according to claim 1, further comprising after said contacting step, the step of rectifying the hydrogen fluoride phase in a rectifying column to obtain purified hydrogen fluoride.

7. A process according to claim 6, wherein said rectifying step is carried out in a rectifying column at a head temperature of from 10 to 20° C. at the top of the column and a base temperature of from 160 to 200° C. at the bottom of the column.

8. A process for producing a fluorine-containing hydrocarbon, said process comprising:
reacting a halogenated hydrocarbon containing a halogen other than fluorine with excess hydrogen fluoride to effect halogen-fluorine exchange;
recovering a reaction mixture from said reacting step and separating said reaction mixture into an organic product phase and a hydrogen fluoride phase;
contacting the hydrogen fluoride phase with oleum in order to remove water present therein and obtain dried hydrogen fluoride, and
recycling the dried hydrogen fluoride to said reacting step.

* * * * *